United States Patent [19]

Wang et al.

[11] Patent Number: 4,691,021

[45] Date of Patent: Sep. 1, 1987

[54] AMINOALKYL HYDANTOINS AND GLYCIDYL DERIVATIVES THEREOF

[75] Inventors: Pen C. Wang, Midland, Mich.; Van I. W. Stuart, Missouri City, Tex.; Ronald L. Yates; Steven P. Crain, both of Midland, Mich.

[73] Assignee: The Dow Chemical Company, Midland, Mich.

[21] Appl. No.: 773,960

[22] Filed: Sep. 9, 1985

[51] Int. Cl.$^4$ .................. C07D 405/14; C07D 233/76
[52] U.S. Cl. .................... 548/309; 548/310; 548/312
[58] Field of Search .................. 548/309, 310, 312

[56] References Cited

U.S. PATENT DOCUMENTS

| | | | |
|---|---|---|---|
| 2,569,428 | 9/1951 | Rowland | 548/238 |
| 3,225,060 | 12/1965 | Johnson | 548/310 |
| 3,419,520 | 12/1968 | Campbell et al. | 524/96 |
| 3,449,353 | 6/1969 | Porret et al. | 548/309 |
| 3,631,221 | 12/1971 | Batzer et al. | 528/363 |
| 3,635,844 | 1/1971 | Porret | 528/117 |
| 3,635,845 | 1/1972 | Porret et al. | 528/117 |
| 3,644,365 | 2/1972 | Habermeier et al. | 544/312 |
| 3,697,539 | 10/1972 | Porret et al. | 548/310 |
| 3,725,342 | 4/1973 | Porret et al. | 528/107 |
| 3,821,243 | 2/1974 | Habermeier et al. | 548/310 |
| 3,839,298 | 10/1974 | Habermeier et al. | 528/341 |
| 3,907,719 | 9/1975 | Habermeier et al. | 528/363 |
| 3,925,407 | 12/1975 | Stockinger et al. | 548/309 |
| 3,963,667 | 6/1976 | Schreiber et al. | 528/103 |
| 4,073,927 | 2/1978 | Freilich | 514/389 |
| 4,110,536 | 8/1978 | Havera et al. | 544/139 |
| 4,140,658 | 2/1979 | Seltzer | 528/93 |
| 4,210,744 | 7/1980 | Bateman | 528/363 |
| 4,284,573 | 8/1981 | Arnett et al. | 549/517 |
| 4,367,299 | 1/1983 | Renner et al. | 523/547 |
| 4,465,830 | 8/1984 | Takeuchi et al. | 528/117 |

OTHER PUBLICATIONS

M. Fazio, *Jour. Org. Chem.*, vol. 49, pp. 4889–4893, (1984).

*Primary Examiner*—Richard A. Schwartz

[57] ABSTRACT

Novel aminoalkyl hydantoins and glycidyl derivatives thereof are prepared from previously unknown 3-(amidoalkyl) hydantoins.

19 Claims, No Drawings

AMINOALKYL HYDANTOINS AND GLYCIDYL DERIVATIVES THEREOF

BACKGROUND OF THE INVENTION

The present invention relates to novel aminoalkylimides and the glycidyl ethers of these compounds.

Certain heterocyclic triglycidyl compounds and the advanced derivatives thereof are described in U.S. Pat. No. 3,821,243; U.S. Pat. No. 3,907,719; U.S. Pat. No. 3,963,667; U.S. Pat. No. 3,925,407 and U.S. Pat. No. 4,210,744. U.S. Pat. No. 4,367,299 discloses the tetraglycidyl ether of bisphenol A. U.S. Pat. No. 4,465,830 discloses the use of dihydrazides of hydantoins as curing agents for epoxy resins.

Alkylamino derivatives of 5-(indol-3-yl)hydantoins are disclosed in U.S. Pat. No. 4,110,536. It is known to prepare aminopropyl hydantoins in two steps by reacting acrylonitrile with hydantoin, and then catalytically hydrogenating the resulting cyanoethyl hydantoins to form aminopropyl hydantoins. See, e.g., U.S. Pat. No. 3,635,844; U.S. Pat. No. 3,635,845; U.S. Pat. No. 3,644,365; U.S. Pat. No. 3,697,539; U.S. Pat. No. 3,725,342; and U.S. Pat. No. 4,073,927. U.S. Pat. No. 3,839,298 on its face teaches di(amino(ethyl or propyl)-)hydantoins, depending on whether the variable "a" is 2 or 3. However, all teaching in said patent specifies the acrylonitrile cyanoethylation route mentioned hereinabove, which, of course, cannot be used to directly prepare aminoethyl hydantoins.

U.S. Pat. No. 4,140,658 lists, as examples of secondary amines, some 1,3-bis(alkylaminoalkyl)-5,5-dialkyl hydantoins.

It would be desirable to have aminoethyl hydantoins and related compounds which could be used in the preparation of novel glycidyl-substituted derivatives thereof.

SUMMARY OF THE INVENTION

The present invention is a class of aminoethyl hydantoins and the amine salts and the glycidyl derivatives thereof. These compounds are unique in that they have a two carbon atom linkage between an amino moiety and a hydantoin ring, and in that they have one amino moiety per hydantoin ring. The aminoethyl hydantoins readily can be converted to novel epoxy resins via the addition of, e.g., epichlorohydrin. The novel resins are useful in known epoxy resin applications.

DETAILED DESCRIPTION OF THE INVENTION

Preferred compositions of the present invention comprise at least one compound of one of the following formulas:

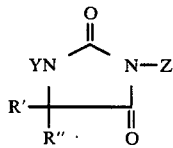
(A)

wherein R' and R" are independently H, lower alkyl or phenyl; wherein Z is a moiety of the formula:

—C(R)$_2$C(R)$_2$N(Q)$_2$ wherein each Q independently is R or a moiety of the formula

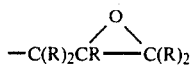

wherein each R independently is H or an aliphatic or inertly-substituted aliphatic moiety of up to about 25 carbon atoms; and wherein Y is H when Q is R, but Y and Q are the same when Q is

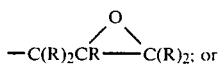

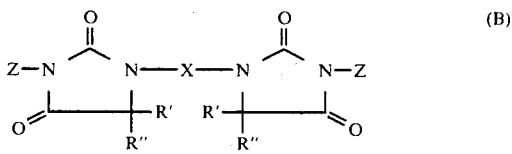
(B)

wherein X is a divalent moiety, and wherein each Z is selected independently.

Preferably, each R independently is H, hydrocarbyl or hydrocarbyl which contains heteroatoms, and typically has up to about 25 carbon atoms. More preferably, each R independently is H or an aliphatic or inertly-substituted aliphatic moiety of up to about 10 carbon atoms including, e.g., lower alkyl. Most preferably, each R is H. R' and R" can combine with their geminal carbon atom to form cyclic moieties, resulting in spiro hydantoins. Said cyclic moieties preferably contain from about 5 to about 7 carbons atoms in the R'—R" ring.

The =CR'R" moiety can be a more complex structure, such as adamantylidene. Preferably, each R' and R" independently is H or lower alkyl of up to about 6 carbon atoms. Examples of lower alkyl moieties include methyl, ethyl, and propyl. Most preferably, each R' and R" is H.

The Z moieties can be identical or different in the bis hydantoin compounds, although it is preferred that each Z is the same in a bis hydantoin.

Typically, X is a divalent hydrocarbyl, e.g., aliphatic, aromatic, or mixed aromatic aliphatic, moiety and can contain heteroatoms such as, for example, sulfur, nitrogen and oxygen. Examples of preferred X bridging moieties include alkylene, alkenylene, cycloalkylene, cycloalkenylene, arylene, and the like, typically of up to about 28 carbon atoms, and preferably of from about 1 to about 10 carbon atoms. For example, the X moiety is methylene in 1,1'-methylene-bis(-3-aminoethyl-(5,5-dimethylhydantoin)).

A. Preparation of the Amines or Amine Salts

The amines of the present invention can be readily prepared by hydrolyzing N-(amidoalkyl)hydantoins of the formulas:

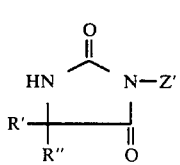

and

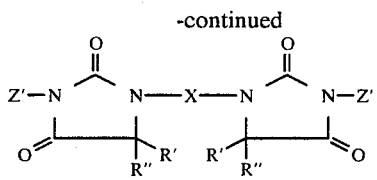

wherein each Z' independently is

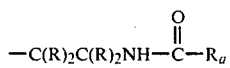

wherein $R_a$ is H, hydrocarbyl of up to about 25 carbon atoms or hydrocarbyl which contains heteroatoms.

For the purposes of the present invention, the term "hydrocarbyl" includes inertly-substituted hydrocarbyl moieties. This also applies to the terms such as alkyl, alkylidene, phenyl, arylene and the like as used herein. For the purposes of the present invention, the term "inert" refers to inertness of a moiety under reaction conditions with respect to the reactive sites of the reactants.

The hydrolysis of the N-(amidoalkyl)hydantoins can be performed using well-known techniques. For an example of a reference to hydrolysis techniques, see M. J. Frazio, *J. Org. Chem.*, Vol. 49, pp. 4889–93 (1984).

B. Preparation of the N-(amidoalkyl)Hydantoins

The N-(amidoalkyl)hydantoins can be readily prepared by contacting a hydantoin and a 2-oxazoline under reaction conditions such that there is formed an N-(amidoalkyl)hydantoin.

Hydantoins are a well-known class of compounds. The hydantoin employed in the preparation of the N-(amidoalkyl)hydantoin can be a mono- or bis hydantoin so long as at least one imide nitrogen atom is bonded to a hydrogen atom. Examples of typical mono hydantoins include 5,5-dimethyl hydantoin, 5-methyl hydantoin, 5,5-diethyl hydantoin, and 5,5-diphenyl hydantoin. As stated hereinabove, when R' and R" are combined, =CR'R" is a cycloalkylidene group and spiro hydantoins are involved. The cycloalkylidene groups preferably contain 5 to 7 carbon atoms in the ring and can be exemplified by cycloheptylidene. Examples of typical bis hydantoins include 1,1'-methylene-bis-(5,5-dimethyl hydantoin); 1,1'-methylene-bis-(5,5-dimethyl hydantoin; bis hydantoins mentioned in U.S. Pat. No. 3,225,060 (which is incorporated herein be reference), and the like.

Preferred 2-oxazolines are represented generally by the formula:

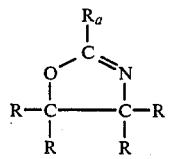

wherein R is as defined hereinabove, and wherein $R_a$ is H, hydrocarbyl, or hydrocarbyl which contains heteroatoms, and typically has up to about 25 carbon atoms. $R_a$ can also represent a link to a second oxazoline ring to form a bis-oxazoline as exemplified by the preferred structure:

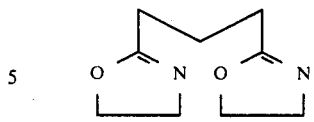

which is disclosed in U.S. Pat. Nos. 2,569,428 and 3,419,520 which are hereby incorporated by reference.

A key aspect is that $R_a$ is inert when it is exposed to other reactants under the reaction conditions. For example, $R_a$ can be hydrogen, methyl, ethyl, undecyl, stearyl, phenyl, benzyl, hydroxyethyl, or p-nitrophenyl. Inert substituents include, for example, the radicals capable of being $R_a$, ethers, thioethers, amides, hydroxy and tertiary amines. $R_a$ preferably is a straight-chain aliphatic radical of 1 to 12 carbon atoms. $R_a$ most preferably is ethyl.

An inert solvent is optionally employed in the process for preparing the N-(amidoalkyl)hydantoin, although it is preferred to operate in the substantial absence of a solvent. Examples of inert solvents include toluene, ethers, and chlorobenzene.

The process can be conducted at any combination of temperature and pressure at which the reaction proceeds. Ambient pressure preferably is employed for the sake of convenience, although sub- or superatmospheric pressure can be employed if desired. The process typically is conducted at a temperature of from about 90° C. to about 150° C.

A catalyst is not required but can be employed if desired. Examples of typical catalysts include protonic acids having non-nucleophilic counterions, onium salts, such as ammonium and phosphonium salts, and Lewis acids. If employed, the catalyst is employed in a catalytic amount. Typically, less than about 5 mole percent of the catalyst, per mole of oxazoline, if employed.

The preferred catalysts are Lewis acids. Lewis acids are well-known to those skilled in the art and are generally defined as a substance that can take up an electron pair to form a covalent bond. Representative examples include $BF_3$, $AlCl_3$, $SnCl_4$, $ZnCl_2$, $FeCl_2$, $H_2WO_3$, $Fe_2SO_4$, $Zn(O_2CCH_3)_2$, $CdCl_2$, $CoCl_2$, and $I_2$. Protonic acids with non-nucleophilic counterions or anions are also a known class of compounds. Protonic acids contain hydrogen. Representative examples include p-toluenesulfonic acid, sulfuric acid and phosphoric acid.

When a hydantoin and a 2-oxazoline are contacted as described herein, a corresponding N-(amidoalkyl)-hydantoin is formed. The exact structure of the product hydantoin is a function of the reactants and stoichiometry employed. For example, a diimido reactant can be reacted with 2 moles of oxazoline. In the simplest case, a monoimide is contacted with a mono-oxazoline. It is preferred to employ the oxazoline and the imido reactant in the stoichiometric amounts required to obtain the desired imide product. Nonstoichiometric amounts can be employed if desired. The reaction of a monoimido reactant with a mono-oxazoline is exemplified as follows:

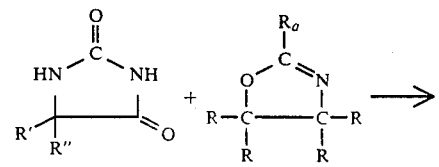

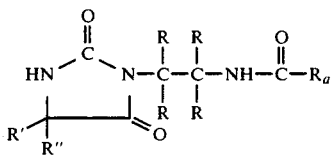

C. Preparation of Hydantoin Epoxy Resins

The hydantoin epoxy resins of the present invention are prepared by contacting an aminoalkyl hydantoin of the present invention or a salt thereof with a haloalkylene oxide under reaction conditions such that there is formed a hydantoin epoxy resin of the formulas given hereinabove.

Examples of the haloalkylene oxides desirably employed in the process include chloropropylene oxide, chlorobutylene oxide, bromopropylene oxide, and the like of up to about 5 carbon atoms, with chloropropylene oxide (epichlorohydrin) being preferred.

The reaction conditions employed for the addition of haloalkylene oxides to hydroxyl-containing or thiol-containing compounds are well-known. See, e.g., *Handbook of Epoxy Resins*, by Lee and Neville, McGraw-Hill (1967); and U.S. Pat. No. 4,284,573; the teachings of each of which are incorporated herein by reference. The corresponding reaction between haloalkylene oxides and the nitrogenous hydrogens of hydantoins is also known. See, e.g., U.S. Pat. Nos. 3,449,353 and 3,631,221; the teachings of each of which are incorporated by reference herein. Said known conditions are advantageously employed in the preparation of the compounds of the present invention. Typically, for example, from about 3 to about 50 moles of haloalkylene oxide are employed per mole of active hydrogen atoms in the hydantoin, with a preferred amount being from about 10 to about 25 moles per mole. Larger or smaller amounts can be employed if desired. The contacting can be performed at any combination of temperature and pressure at which the desired reaction will proceed. Typically, the contacting is performed at elevated temperature. Preferably, the temperature is from about 60° C. to about the boiling point of the haloalkylene oxide. Ambient pressure is preferred for the sake of convenience.

A catalyst is advantageously employed, and can be selected from known catalysts for this reaction, including the wide range of catalysts mentioned in the references cited previously herein. Examples of preferred catalysts include, for example, tetraethylammonium bromide, ethyltriphenyl phosphonium acetate and the like.

The tris- and tetraepoxy resins of the present invention can be cured to form novel epoxy polymers having surprisingly improved properties. The epoxy resins can be cured using well-known techniques. The novel cured resins of the present invention typically are prepared by heating the polyepoxide compounds with a curing agent, typically at a temperature of from about 0° C. to about 300° C., and preferably from about 25° C. to about 250° C.

As curing agents there can, for example, be mentioned: amines or amides such as aliphatic, cycloaliphatic or aromatic primary, secondary and tertiary amines, for example, monoethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3, bis(4'-amino-3-methylcyclohexyl)methane, 2,2-bis(4'-aminocyclohexyl)propane, 3,5,5-trimethyl-3-(aminomethyl)cyclohexylamine ("isophoronediamine"), N-aminoethylpiperazine, Mannich bases, such as 2,4,6-tris(dimethylaminomethyl)phenol; m-phenylenediamine, p-phenylenediamine, bis(p-aminophenyl)-methane, bis(p-aminophenyl)sulfone and m-xylylenediamine; adducts of acrylonitrile or monoepoxides such as ethylene oxide or propylene oxide to polyalkylenepolyamines such as diethylenetriamine or triethylenetetramine; adducts of polyamines such as excess diethylenetriamine or triethylenetetramine, and polyepoxides such as diomethane polyglycidly ethers; ketimines, for example, from acetone or methyl ethyl ketone and bis(p-aminophenyl)methane; adducts of monophenols or polyphenols and polyamines; polyamides, especially those from aliphatic polyamines, such as diethylenetriamine or triethylenetetramine and dimerized or trimerized unsaturated fatty acids such as dimerized linseed oil fatty acid ("VERSAMID"); polymeric polysulfides ("THIOKOL"); dicyandiamide; aniline-formaldehyde resins; polyhydric phenols, for example, resorcinol, 2,2-bis(4-hydroxyphenyl)propane or phenol-formaldehyde resins; boron trifluoride and its complexes with organic compounds, such as $BF_2$ ether complexes and $BF_3$ amine complexes, for example, $BF_3$-monoethylamine complex; acetoneacetanilide-$BF_3$ complex; phosphoric acid, triphenylphosphite, polybasic carboxylic acids and their anhydrides, for example, phthalic anhydride, tetrahydrophthalic anhydride, hexahydrophthalic anhydride, 4-methylhexahydrophthalic anhydride, 3,6-endomethylene-tetrahydrophthalic anhydride, methyl-3,6-endomethylene-tetrahydrophthalic anhydride, (methylnadicanhydride), 3,4,5,6,7,7-hexachlor-3,6-endomethylene-tetrahydrophthalic anhydride, succinic anhydride, adipic anhydride, azelaic anhydride, sebacic anhydride, maleic anhydride, dodecenyl-succinic anhydride; pyromellitic dianhydride or mixtures of such anhydrides.

It is particularly advantageous to use curing agents which in themselves yield molding materials of good electrical properties, such as especially cycloaliphatic dicarboxylic acid anhydrides such as, for example, $\Delta^4$-tetrahydrophathalic anhydride or hexahydrophthalic anhydride, or cycloaliphatic polyamines such as, for example, 2,2-bis(4'-aminocyclohexyl)propane or "isophoronediamine".

It is furthermore possible to use cure accelerators during the cure, and in particular when using polyamides, polymeric polysulfides, dicyandiamide or polycarboxylic acid anhydrides as curing agents; such accelerators are, for example, tertiary amines, their salts or quaternary ammonium compounds, for example, 2,4,6-tris(-dimethylaminomethyl)phenol, benzyldimethylamines, 2-ethyl-4-methylimidazole or triamylammonium phenolate; or alkali metal alcoholates such as, for example, sodium hexanetriolate.

The expression "cure" as used here denotes the conversion of the above adducts containing epoxide groups into insoluble and infusible cross-linked products, and in particular as a rule with simultaneous shaping to give shaped articles such as castings, pressings or laminates, or to give two-dimensional structures such as coatings, lacquer films or adhesive bonds.

If desired, it is possible to add active diluents such as, for example, styrene oxide, butylglycidyl ether, isooctylglycidyl ether, phenylglycidyl ether, cresylglycidyl ether or glycidyl esters of synthetic highly branched mainly tertiary aliphatic monocarboxylic acids ("CARDURA E"), or cycloaliphatic monoepoxides such as 3-vinyl-2,4-dioxaspiro (5,5)-9,10-epoxyundecane.

The adducts according to the invention can furthermore be mixed with other curable diepoxide or polyepoxide compounds. As such that can, for example, be mentioned: polyglycidyl ethers of polyhydric alcohols such as 1,4-butanediol, polyethylene glycols, polypropylene glycols or 2,2-bis(4'-hydroxycyclohexyl)propane; polyglycidyl ethers of polyhydric phenols such as 2,2-bis(4'-hydroxyphenyl)-propane, 2,2-bis(4'-hydroxy-3,5'-dibromophenyl)-propane, bis(4-hydroxyphenyl)sulfone, 1,1,2,2-tetrakis(4-hydroxyphenyl)ethane or condensation products of formaldehyde with phenols produced in an acid medium, such as phenol novolacs or cresol novolacs; polyglycidyl esters of polycarboxylic acids such as, for example, phthalic acid diglycidyl ester, tetrahydrophthalic acid diglycidyl ester or hexahydrophthalic acid diglycidyl ester; triglycidyl isocyanurate, N,N'-diglycidyl-5,5-dimethyl hydantoin, or aminopolyepoxides such as are obtained by dehydrohalogenation of the reaction products of epihalogenohydrin and primary or secondary amines such as aniline or 4,4'-diaminodiphenylmethane; also alicyclic compounds containing several epoxide groups, such as vinylcyclohexane-diepoxide, dicyclopentadienediepoxide, ethylene glycol-bis(3,4-epoxytetrahydrodicylopentadien-8-yl)ether, (3,4-epoxycyclohexylmethyl)-3,4-epoxycyclohexanecarboxylate, (3',4'-epoxy-6'-methylcyclohexylmethyl)-3,4-epoxy-6-methylcyclohexanecarboxylate, bis(cyclopentyl)ether diepoxide or 3-(3',4'-epoxycyclohexyl)-2,4-dioxaspiro-(5,5)9,10-epoxyundecane.

The subject of the present invention therefore also includes curable mixtures which are suitable for the manufacture of shaped articles including two-dimensional structures and which contain the so-called "advanced" adducts containing epoxide groups according to the invention, optionally together with other diepoxide or polyepoxide compounds and also curing agents for epoxide resins such as polyamines or polycarboxylic acid anhydrides.

The compounds of the invention, or their mixtures with other polyepoxide compounds and/or curing agents, can furthermore be mixed, at any state before cure, with usual modifiers such as extenders, fillers and reinforcing agents, pigments, dyestuffs, organic solvents, plasticizers and the like.

As extenders, reinforcing agents, fillers and pigments which can be employed in the curable mixtures according to the invention there can, for example, be mentioned: coal tar, bitumen, glass fibers, boron fibers, carbon fibers, cellulose, polyethylene powder, polypropylene powder, mica, asbestos, quartz powder, slate powder, aluminum oxide trihydrate, chalk powder, gypsum, antimony trioxide, bentones, silica aerogel ("AEROSIL"), lithiopone, barite, titanium dioxide, carbon black, graphite, iron oxide or metal powder such as aluminum powder or iron powder.

The following are, for example, suitable as organic solvents for modifying the curable mixtures: toluene, xylene, n-propanol, butyl acetate, acetone, methyl ethyl ketone, diacetone-alcohol, ethylene glycol, monomethyl ether, monoethyl ether and monobutyl ether.

Dibutyl, dioctyl and dinonyl phthalate, tricresyl phosphate, trixylenyl phosphate and also polypropylene glycols can, for example, be employed as plasticizers for modifying the curable mixtures.

Especially for use in the lacquer field, the new adducts containing epoxide groups can furthermore be partially or completely esterified in a known manner with carboxylic acids, such as especially higher unsaturated fatty acids. It is furthermore possible to add other curable synthetic resins, for example, phenoplastics or aminoplastics, to such lacquer resin formulations.

It is furthermore also possible to add other usual additives, for example, flame-proofing agents, agents for conferring thixotropy, flow control agents such as silicones, cellulose acetobutyrate, polyvinyl butyral, waxes, stearates and the like (which are in part also used to mold release agents) to the curable mixtures.

The curable mixtures can be manufactured in the usual manner with the aid of known mixing equipment (stirrers, kneaders, rollers and the like).

The curable epoxide resin mixtures above are all employed in the fields of surface protection, the electrical industry, laminating processes and the building industry. They can be used in a formulation which is in each case suited to the particular end use, in the unfilled or filled state, optionally in the form of solutions of emulsions, as paints, lacquers, sintering powders, compression molding compositions, dipping resins, casting resins, injection molding formulations, impregnating resins and adhesives, as tool resins, laminating resins, sealing and filling compositions, floor covering compositions and binders for mineral aggregates.

A main field of application lies in the field of compression molding powders and of sintering powders. Here the epoxide resin powder mixtures can be processed without pressure or with pressure, according to known processes such as fluidized bed sintering, electrostatic fluidized bed sintering, spraying, electrostatic spraying, compression molding and the like.

SPECIFIC EMBODIMENTS

The following preparations, examples and comparative experiments are intended to illustrate the invention and should not be construed as limiting its scope. All parts and percentages are by weight unless otherwise indicated.

PREPARATION 1

3-(2-propionamidoethyl)-5,5-dimethyl hydantoin; also called
N-(2-(4,4-dimethyl-2,5-dioxoimidazolidinyl)ethyl)propane amide A mixture of 0.1 mole (12.8 g) of 5,5'-dimethyl hydantoin and 0.1 mole (9.9 g) of 2-ethyl-oxazoline is placed in a 100-ml round-bottom flask equipped with a condensing means, a heating means, and a stirring means. The mixture is heated with stirring to 130° C. The progress of the reaction is monitored by proton nuclear magnetic resonance spectroscopy or gas liquid chromatography, and the reaction time is about 6 hours. The product is isolated by recrystallization from a mixture of ethyl acetate and methanol, and its structure is confirmed by nuclear magnetic resonance spectral data and elemental analysis as being that of the title compound. The isolated yield is approximately 90 percent, and the product has a melting point of 128° C.-129° C.

PREPARATION 2

1,1'-methylene-bis(3-(2-propionamidoethyl)-5,5-dimethyl hydantoin)

The procedure of Preparation 1 is repeated using 1,1'-methylene-bis-(5,5-dimethyl hydantoin) as the hydantoin and twice as much of the oxazoline to produce the title compound in an isolated yield of 75 percent.

EXAMPLE 1

3-(2-monohydrochloride aminoethyl)-5,5-dimethyl hydantoin

A mixture of 130.3 g (0.576 mole) of the product of Preparation 1, 95 ml (1.16 moles) of concentrated HCl, and 300 ml $H_2O$ is added to a 1-liter round-bottom flask equipped with means for stirring condensing, and heating. The contents of the flask are heated with stirring to reflux temperature, which is maintained for 12 hours. The contents are then concentrated under reduced pressure to remove water the propionic acid. The resulting slurry is added to 100 ml of methanol and the resulting white crystals are filtered and dried to give a 97 percent isolated yield of crystals having a melting point of 199° C.–201° C. The structure of the title compound is confirmed using proton nuclear magnetic resonance spectroscopy.

Example 1 demonstrates the preparation of a salt of an amine of the present invention.

EXAMPLE 2

The product of Preparation 2 (232.3 g, 0.50 mole) and 83.3 ml of concentrated HCl in 500 ml of water, are placed in a 2-liter flask equipped with means for condensing, heating, and stirring. The mixture is heated to reflux, 100° C., with stirring. It is maintained at reflux with stirring for 12 hours. Water and propionic acid are then removed under reduced pressure. The resulting diethylamine hydrochloride salt is washed with 100 ml of methanol, and is dried. The yield is 80 percent, and the melting point of the diamine salt is 272 C.–275° C.

The diamine hydrochloride salt is dissolved in water and 2 equivalents of NaOH are added to the solution. The water is removed under reduced pressure and the free amine, 1,1'-methylene-bis(3-N-(2-aminoethyl)-5,5'-dimethyl hydantoin), is dissolved in methanol to precipitate NaCl. The methanol is then removed under reduced pressure to give a 100 percent yield of the diamine, which has a melting point of 103° C.

The structures of compounds formed in this example are confirmed by proton nuclear magnetic resonance spectroscopy.

EXAMPLE 3

1-glycidyl-3-(2-diglycidylaminoethyl)-5,5-dimethyl hydantoin

To a 1-liter round-bottom flask equipped with a stirring means, a dropping funnel, and a water separator for circulation-distillation, is added a mixture of 24.32 g (0.117 mole) of the hydrochloride salt prepared in Example 1, 150 ml (1.92 moles) of epichlorohydrin, 225 ml of toluene and 2 g of tetraethylammonium bromide. The mixture is stirred for four hours at 90° C., and then is allowed to cool. The pressure in the flask is then reduced to 50 mm Hg and the temperature is increased to 45° C. Then, 37.52 g of 50 weight percent aqueous sodium hydroxide (0.469 mole) is added over a period of 30 minutes with the azeotropic removal of water. When the addition of sodium hydroxide is complete, the distillation is continued for an additional 60 minutes with circulation of epichlorohydrin. The reaction mixture is then cooled to 40° C. and the precipitated sodium chloride is removed by suction filtration. The epichlorohydrin solution is washed with 50 ml of $H_2O$ and is concentrated under reduced pressure to dryness to give a 90 percent yield of the title triglycidyl compound having 96.5 g per epoxy equivalent (which is 85 percent of the theoretical 113 g per epoxy equivalent). The calculated elemental analysis is as follows: carbon 56.64, hydrogen 7,37, nitrogen 12.39. The observed elemental analysis is as follows: carbon 56.10, hydrogen 7.36, and nitrogen 12.12. The structure is confirmed by proton nuclear magnetic resonance spectroscopy.

EXAMPLE 4

1,1'-methylene-bis(3'',3'''-(2-diglycidlyaminoethyl)-5,5-dimethyl hydantoin)

To a 3-liter round-bottom flask equipped in the same manner as the flask of Example 3 is added a mixture of 200 g (0.47 mole) of the intermediate product of Example 2: 1,1'-methylene-bis(3-N-(2-aminoethyl)-5,5-dimethyl hydantoin).2HCl, along with 850 ml (12.8 moles) of epichlorohydrin and 5 g of tetraethylammonium bromide. The mixture is stirred for 30 minutes at 80° C. Then, 400 ml of a mixture of 75 volume percent methyl ethyl ketone and 25 volume percent toluene is added to the mixture. The pressure in the vessel is then reduced to 50 mm Hg and the temperature is reduced to 50° C. Then, 225 g of a 50 weight percent aqueous solution of sodium hydroxide is added over a period of 45 minutes with the azeotropic removal of water. Following the addition of sodium hydroxide, the distillation is continued for an additional 60 minutes with circulation of epichlorohydrin. The reaction mixture is then cooled to 40° C. and the precipitated sodium chloride is removed by suction filtration. The epichlorohydrin solution is washed with 50 ml of water and is concentrated under reduced pressure to dryness to give a 95 percent yield of the title tetraglycidyl compound having an epoxy equivalent weight of 106 g per epoxy equivalent. The structure is confirmed by proton nuclear magnetic resonance spectroscopy.

EXAMPLE 5

The trisglycidyl hydantoin of Example 3 is heated to 100° C. in a vacuum of approximately 1 mm Hg for 2 hours. Then, an amount of bis(4-aminophenyl)sulfone is added so that there is one epoxy moiety per each amine active hydrogen. The resulting mixture is stirred and is poured into aluminum pans and placed in a vacuum oven at 140° C. for 6.5 hours. The mixture gels into a translucent orange disk. The orange disk is post-cured by heating it to 180° C. for 2 hours and then cooling at 100° C. for 6.75 hours. The $T_g$ (glass transition temperature) of the cured material is found to be 190° C. by differential scanning calorimetry (hereinafter DSC).

EXAMPLE 6

A mixture of 0.26 mole of the tetraglycidyl epoxy resin of Example 4 (106 g per epoxide equivalent, 92 percent of theoretical) and 0.23 mole of methylenedianiline is heated and stirred at 125° C. until most of the methylenedianiline is dissolved. The mixture is then degassed and poured into preheated molds at 125° C. and the molds are placed in an oven for 2 hours at 125°

C. and then 2 hours at 175° C. The molded articles have the following properties: glass transition temperature ($T_g$): 150° C.; decomposition (percent weight loss at 300° C.): 6 percent, young modulus, PSI: $6.4 \times 10^5$; impact strength, ft-lb/in.: $0.39 \pm 0.26$.

EXAMPLE 7

A mixture of 0.335 mole of the tetraglycidyl resin of Example 4 and 0.288 mole of diaminodiphenylsulfone, is heated and stirred at 150° C. until most of the diaminodiphenylsulfone is dissolved. The mixture is then degassed and poured into preheated molds at 150° C. and is allowed to gel ($\approx \frac{1}{2}$ hour). The molds are placed in an oven for 2 hours at 150° C. and then for 2 hours at 180° C. The molded articles have the following properties: glass transition temperature ($T_g$): 192° C.; decomposition (percent weight loss at 300° C.): 6 percent.

What is claimed is:

1. A compound of one of the following formulas:

wherein R' and R" are independently H, lower alkyl or phenyl, and wherein Z is a moiety of the formula:

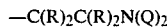

—C(R)$_2$C(R)$_2$N(Q)$_2$ wherein each Q independently is R or a moiety of the formula:

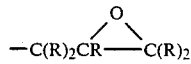

wherein each R independently is H or an aliphatic or inertly-substituted aliphatic moiety of up to about 25 carbon atoms, wherein inertness is defined as inertness with respect to reactive sites of the reagents under reaction conditions; and wherein Y is H when Q is R, but Y and Q are the same when Q is

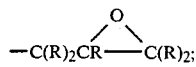

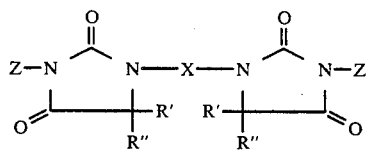

wherein X is a divalent hydrocarbyl moiety which contains zero, one or more hetero atoms, and wherein each X is selected independently, provided that when X does not contain a hetero atom then Z contains the

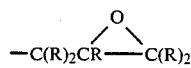

group.

2. A hydantoin of claim 1 wherein each Q is H or a moiety of the formula:

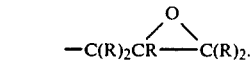

3. A hydantoin of claim 1 wherein each R is H.
4. A hydantoin of claim 1 wherein each R independently is H or an aliphatic or inertly-substituted aliphatic moiety of up to about 10 carbon atoms.
5. A hydantoin of claim 1 wherein Q is R.
6. A hydantoin of claim 2 wherein Q is represented by the formula:

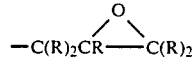

and each R is H or an aliphatic or inertly substituted aliphatic moiety of up to about 10 carbons.

7. A trisepoxy hydantoin of claim 1 wherein Y and Q are

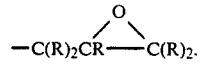

8. A hydantoin of claim 7 wherein each R is H.
9. A hydantoin of claim 8 wherein each R' and R" independently is H, methyl, ethyl or propyl.
10. A hydantoin of claim 9 wherein each R' and R" is H.
11. A hydantoin of claim 1 wherein X is methylene.
12. A hydantoin of claim 11 wherein each R is H.
13. A hydantoin of claim 11 wherein each R' and R" is H.
14. A hydantoin of claim 12 wherein each R' and R" is H.
15. An amino alkyl hydantion of the following formula:

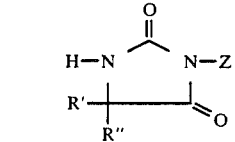

wherein R' and R" are independently H, lower alkyl or phenyl, and wherein Z is an aminoalkyl moiety of the formula:

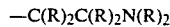

—C(R)$_2$C(R)$_2$N(R)$_2$ wherein each R independently is H, or an aliphatic or inertly-substituted aliphatic moiety of up to about 10 carbon atoms and wherein inertness is defined as inertness with respect to reactive sites of the reagents under reaction conditions.

16. A hydantoin of claim 15 wherein each R' and R" is H.
17. A hydantoin of claim 15 wherein each R bonded to a carbon atom is H.
18. A hydantoin of claim 15 wherein each R is H.
19. A hydantoin of claim 15 wherein each R' and R" is independently H, methyl, ethyl or propyl.

* * * * *